(12) United States Patent
Lenn et al.

(10) Patent No.: US 10,251,885 B2
(45) Date of Patent: Apr. 9, 2019

(54) AZOLE ANTIFUNGAL COMPOSITIONS

(75) Inventors: Jon Lenn, Research Triangle Park, NC (US); Hans Hofland, Research Triangle Park, NC (US); Edward Hsia, Palo Alto, CA (US)

(73) Assignee: ALLERGAN PHARMACEUTICALS INTERNATIONAL LIMITED, Dublin (IE)

( * ) Notice: Subject to any disclaimer, the term of this patent is extended or adjusted under 35 U.S.C. 154(b) by 452 days.

(21) Appl. No.: 13/322,667

(22) PCT Filed: May 27, 2010

(86) PCT No.: PCT/US2010/036331
§ 371 (c)(1),
(2), (4) Date: Feb. 8, 2012

(87) PCT Pub. No.: WO2010/138674
PCT Pub. Date: Dec. 2, 2010

(65) Prior Publication Data
US 2012/0128612 A1 May 24, 2012

Related U.S. Application Data (60) Provisional application No. 61/213,335, filed on May 29, 2009, provisional application No. 61/239,811, filed on Sep. 4, 2009.

(51) Int. Cl.
*A61K 31/517* (2006.01)
*A61K 9/00* (2006.01)
*A61K 9/70* (2006.01)
*A61K 45/06* (2006.01)

(52) U.S. Cl.
CPC .......... *A61K 31/517* (2013.01); *A61K 9/0014* (2013.01); *A61K 9/7015* (2013.01); *A61K 45/06* (2013.01)

(58) Field of Classification Search
CPC .. A61K 9/0014; A61K 9/7015; A61K 31/517; A61K 45/06
USPC ............................ 424/61; 514/167, 171, 266
See application file for complete search history.

(56) References Cited

U.S. PATENT DOCUMENTS

| 4,957,730 | A | | 9/1990 | Bohn et al. |
|---|---|---|---|---|
| 5,807,854 | A | * | 9/1998 | Bartroli et al. ............. 514/248 |
| 6,042,845 | A | * | 3/2000 | Sun ................... A61F 13/105 |
| | | | | 424/446 |
| 6,231,875 | B1 | | 5/2001 | Sun et al. |
| 7,588,753 | B2 | * | 9/2009 | Ferrandis et al. ............. 424/61 |
| 7,879,867 | B2 | | 2/2011 | Paredes et al. |
| 2008/0076787 | A1 | * | 3/2008 | Paredes et al. .......... 514/266.23 |
| 2008/0220103 | A1 | | 9/2008 | Birnbaum et al. |

FOREIGN PATENT DOCUMENTS

| JP | 10-508317 A | 8/1998 |
|---|---|---|
| JP | 2002-509867 A | 4/2002 |
| JP | 2002-520283 A | 7/2002 |
| JP | 2004-529923 A | 9/2004 |
| JP | 2005-538156 A | 12/2005 |
| WO | 2010-108060 A | 9/2010 |
| WO | 2010/108060 A1 | 9/2010 |

OTHER PUBLICATIONS

Sheehan et al, Title: Current and emerging azole antifungal agents, Clin. Mircobiol. Rev., Jan. 1999, p. 40-79.*
Sorbera et al., "Albaconazole: antifungal," Drugs of the Future, Prous Science, ES, vol. 28, No. 6, Jan. 1, 2003), pp. 529-537, XP002461045, ISSN: 0377-8282, DOI: 10.1358/DOF.2003.028.06. 738951.
Hsia et al., "Models for the development of topical products for the treatment of onychomycosis," Journal of Investigative Dermatology, 39th Annual Meeting of the European Society for Dermatological Research, Nature Publishing Group, GB, Budapest, Hungary, vol. 129, no. Suppl. 2, Sep. 1, 2009, p. S102, XP008157028, ISSN: 022-202X, DOI: 10.1038/JID.2009.232.
Supplementary European Search Report dated Oct. 23, 2012 in co-pending European application No. 10781187.9.
Japanese Office Action, English translation enclosed.
B.F. Torres et al., Antimicrobial Agents and Chemotherapy, 2001, vol. 45, No. 9, p. 2524-2528.
A.R. Welshenbaugh et al., Abstracts of the Interscience Conference on Antimicrobial Agents and Chemotherapy, 2007, vol. 47, p. 451, "M-1814".

* cited by examiner

*Primary Examiner* — Yanzhi Zhang
(74) *Attorney, Agent, or Firm* — Nath, Goldberg & Meyer; Joshua B. Goldberg; Scott H. Blackman (57) ABSTRACT

The present invention relates generally to antifungal compositions. In an embodiment, the antifungal compositions are effective for application to nails and surrounding skin, and comprise at least one volatile solvent, at least one film forming substance, and at least one pyrimidone derivative of formula I, such as albaconazole. These compositions are capable of treating an infection caused by fungi, such as onychomychosis.

16 Claims, 2 Drawing Sheets

AZOLE ANTIFUNGAL COMPOSITIONS

This is a National Phase Application filed under 35 U.S.C. § 371 as a national stage of International Application No. PCT/US2010/036331, filed on May 27, 2010, claiming the benefit under 35 U.S.C. § 119(e) of U.S. Patent Application No. 61/213,335, filed on May 29, 2009, and claiming the benefit under 35 U.S.C. § 119(e) of U.S. Patent Application No. 61/239,811, filed on Sep. 4, 2009, the content of each of which is hereby incorporated by reference in its entirety.

FIELD OF THE INVENTION

The present invention relates to methods of topically treating or preventing an infection caused by fungi.

BACKGROUND OF THE INVENTION

Fungal infections of the nail (known as onychomycosis) and surrounding skin are unsightly and, in certain cases, can result in loss of the nail. These infections are caused by dermatophytes, *Candida* and non-dermatophytic moulds. Common dermatophytes which infect the nail and surrounding skin include *Trichophyton rubrum* and *Trichophyton mentagrophytes*.

Current treatment options for onychomycosis include oral treatment with terbinafine, itraconazole, griseofulvin or fluconazole. Alternative options include topical treatment with amorolfine or ciclopirox. One such topical composition is described in U.S. Pat. No. 4,957,730 to Bohn et al. which discloses a nail varnish comprising a film forming substance and a 1-hydroxy-2-pyridone derivative (such as ciclopirox).

U.S. Pat. No. 6,455,592 to Laugier et al. describes a composition comprising a pharmacologically-effective amount of terbinafine hydrochloride, a solvent medium comprising water and at least one straight- or branched-chain $C_2$-$C_8$ alkanol, and a hydrophilic penetration agent.

US published patent application no. 2003/0190340 to Bohn et al. discloses a preparation comprising a hydrophilic gel-forming agent, water and a compound such as 1-hydroxy-4-methyl-6-cyclohexyl-2(1H)pyridone.

US published patent application no. 2004/0028721 to Colombo et al. discloses single-layer films for the dermal or transdermal administration of active ingredients comprising at least an active ingredient, a film forming agent and a hydrophilic adhesive polymer.

U.S. Pat. No. 5,807,854 to Bartroli et al. describes novel pyrimidone derivatives, such as albaconazole, showing activity against *Candida albicans, Candida krusei* and *Aspergillus fumigatus*.

WO 2008/021049 to Paredes et al. describes novel crystalline forms of albaconazole, namely crystalline Forms I, II, III, IV, V and VI.

There remains a need in the art for methods of topically treating or preventing onychomycosis and other fungal infections of the skin. The present invention addresses these needs.

SUMMARY OF THE INVENTION

One aspect of the present invention provides for a method of treatment, or prophylaxis, of a fungal condition in a human patient, the method comprising topically applying to the patient a pharmaceutically acceptable composition comprising a therapeutically effective amount of a pyrimidone derivative of the general formula I:

as a racemate, a diastereomer mixture or as a pure enantiomer, wherein:

Ar represents phenyl or phenyl substituted with one or more halogen and/or trifluoromethyl groups;

$R_1$ is $C_1$-$C_4$ alkyl;

$R_2$ is hydrogen or $C_1$-$C_4$ alkyl; or $R_1$ together with $R_2$ form a $C_2$-$C_4$ polymethylene chain;

$R_3$ represents hydrogen, $C_1$-$C_4$ alkyl, $C_1$-$C_4$ haloalkyl, or cyclopropyl;

A represents a benzene ring or a 5- or 6-membered heterocyclic ring wherein one or more of the ring atoms are selected from the group consisting of N, O and S, which rings can be optionally fused to a benzene ring or to a 5- or 6-membered heterocyclic ring containing one or more heteroatoms selected from N, O and S, and wherein A can be unsubstituted or have 1, 2, 3 or 4 groups W on any of the rings;

the group W represents $C_1$-$C_4$ alkyl, $C_3$-$C_6$ cycloalkyl, $C_1$-$C_4$ haloalkyl, $C_1$-$C_4$ alkoxy, $C_1$-$C_4$ haloalkoxy, halogen, nitro, cyano, hydroxy, benzyloxy, hydroxymethyl, a —$NR_4R_5$, —$CONR_4R_5$, —$CH_2$—OCO—$R_4$, —CO—$R_4$, —COO—$R_4$, —$SO_zR_6$, —C(=$NR_4$)$NHR_7$, —C(=$NR_7$)$OR_4$, and additionally one of the groups W can also represent 1-pyrrolyl, 1-imidazolyl, 1H-1,2,4-triazol-1-yl, 5-tetrazolyl (optionally substituted with $C_1$-$C_4$ alkyl), 1-pyrrolidinyl, 4-morpholinyl, 4-morpholinyl-N-oxide, a group —X—$R_8$, or a group of formula (i)-(iv):

(i)

(ii)

(iii)

-continued wherein:
R₄ represents hydrogen, $C_1$-$C_4$ alkyl, $C_3$-$C_6$ cycloalkyl or aryl$C_{1-4}$ alkyl, wherein aryl represents phenyl or phenyl substituted with one or more $C_1$-$C_4$ alkyl, halogen, $C_1$-$C_4$ haloalkyl, $C_1$-$C_4$ alkoxy or $C_1$-$C_4$ haloalkoxy;
R₅ represents hydrogen, $C_1$-$C_4$ alkyl, $C_3$-$C_6$ cycloalkyl, —COR₄ or —COCF₃;
R₆ represents $C_1$-$C_4$ alkyl;
R₇ represents hydrogen, —CONH₂, —COMe, —CN, —SO₂NHR₄, —SO₂R₄, —OR₄, —OCOR₄ or —($C_{1-4}$ alkyl)-NH₂;
X represents a single bond, —O—, —SOn, —NR₄—, or —C(=O)—;
n represents 0, 1 or 2;
R₈ represents phenyl or a phenyl substituted with one or more groups R₉;
R₉ represents $C_1$-$C_4$ alkyl, $C_3$-$C_6$ cycloalkyl, $C_1$-$C_4$ haloalkyl, $C_1$-$C_4$ alkoxy, $C_1$-$C_4$ haloalkoxy, halogen, nitro, cyano, —NR₄R₅, —CONR₄R₅, —CH₂—OCO—R₄, —CO—R₄, —COO—R₄, —SO$_z$R₆, —C(=NR₄)NHR₇, —C(=NR₇)OR₄, a group of formula (iv) or R₉ represents phenyl or phenyl optionally substituted with $C_1$-$C_4$ alkyl, $C_1$-$C_4$ haloalkyl, $C_1$-$C_4$ alkoxy, $C_1$-$C_4$ haloalkoxy, halogen, nitro or cyano;
R₁₀ represents hydrogen or methyl;
R₁₁ represents hydrogen, isopropyl, cyclopentyl, cyclopropyl, 2-butyl, 3-pentyl, 3-hydroxy-2-butyl, or 2-hydroxy-3-pentyl;
m represents 0 or 1;
R₁₂ represents halogen, $C_1$-$C_4$ haloalkyl, $C_1$-$C_4$ haloalkoxy, nitro, amino, cyano, or a group of formula (i);
Y represents —CH₂— or —C(=O)—; and
Z represents NH or 0;
and the salts and solvates thereof;
and a pharmaceutically acceptable carrier or diluent thereof, and optionally a second pharmaceutically active agent.

According to another aspect, the present invention provides a topical pharmaceutical composition for the treatment or prophylaxis of a fungal condition, comprising a therapeutically effective amount of a pyrimidone derivative of the general formula I, and a pharmaceutically acceptable carrier or diluent thereof, and optionally a second pharmaceutically active agent.

According to a further aspect, the present invention relates to the use of the compositions described herein for the preparation of a medicament for the treatment or prophylaxis of a fungal condition.

According to yet a further embodiment, the present invention relates to the use of the compositions described herein for the treatment or prophylaxis of a fungal condition.

DETAILED DESCRIPTION OF THE INVENTION

According to one aspect, the present invention provides a method for the treatment or prophylaxis of a fungal condition in a patient, the method comprising topically applying to the patient a pharmaceutically acceptable composition comprising a therapeutically effective amount of a pyrimidone derivative of the general formula I:

as a racemate, a diastereomer mixture or as a pure enantiomer, wherein:

Ar represents phenyl or phenyl substituted with one or more halogen and/or trifluoromethyl groups;
R₁ is $C_1$-$C_4$ alkyl;
R₂ is hydrogen or $C_1$-$C_4$ alkyl; or R₁ together with R₂ form a $C_2$-$C_4$ polymethylene chain;
R₃ represents hydrogen, $C_1$-$C_4$ alkyl, $C_1$-$C_4$ haloalkyl, or cyclopropyl;
A represents a benzene ring or a 5- or 6-membered heterocyclic ring wherein one or more of the ring atoms are selected from the group consisting of N, O and S, which rings can be optionally fused to a benzene ring or to a 5- or 6-membered heterocyclic ring containing one or more heteroatoms selected from N, O and S, and wherein A can be unsubstituted or have 1, 2, 3 or 4 groups W on any of the rings;
the group W represents $C_1$-$C_4$ alkyl, $C_3$-$C_6$ cycloalkyl, $C_1$-$C_4$ haloalkyl, $C_1$-$C_4$ alkoxy, $C_1$-$C_4$ haloalkoxy, halogen, nitro, cyano, hydroxy, benzyloxy, hydroxymethyl, a group —NR₄R₅, a group —CONR₄R₅, a group —CH₂—OCO—R₄, a group —CO—R₄, a group —COO—R₄, a group —SO$_z$R₆, a group —C(=NR₄)NHR₇, a group —C(=NR₇)OR₄, and additionally one of the groups W can also represent 1-pyrrolyl, 1-imidazolyl, 1H-1,2,4-triazol-1-yl, 5-tetrazolyl (optionally substituted with $C_1$-$C_4$ alkyl), 1-pyrrolidinyl, 4-morpholinyl, 4-morpholinyl-N-oxide, a group —X—R₈, or a group of formula (i)-(iv):

-continued (ii)

(iii)

(iv)

wherein:
R₄ represents hydrogen, $C_1$-$C_4$ alkyl, $C_3$-$C_6$ cycloalkyl or aryl$C_1$-$C_4$ alkyl, wherein aryl represents phenyl or phenyl substituted with one or more $C_1$-$C_4$ alkyl, halogen, $C_1$-$C_4$ haloalkyl, $C_1$-$C_4$ alkoxy or $C_1$-$C_4$ haloalkoxy groups;
R₅ represents hydrogen, $C_1$-$C_4$ alkyl, $C_3$-$C_6$ cycloalkyl, —COR₄ or —COCF₃;
R₆ represents $C_1$-$C_4$ alkyl;
n represents 0, 1 or 2;
R₇ represents hydrogen, —CONH₂, —COMe, —CN, —SO₂NHR₄, —SO₂R₄, —OR₄, —OCOR₄ or —($C_{1-4}$ alkyl)-NH₂;
X represents a single bond, —O—, —SOn, —NR₄—, or —C(=O)—;
R₈ represents a phenyl group optionally substituted with one or more groups R₉;
R₉ represents $C_1$-$C_4$ alkyl, $C_3$-$C_6$ cycloalkyl, $C_1$-$C_4$ haloalkyl, $C_1$-$C_4$ alkoxy, $C_1$-$C_4$ haloalkoxy, halogen, nitro, cyano, —NR₄R₅, —CONR₄R₅, —CH₂—OCO—R₄, —CO—R₄, —COO—R₄, —SO₂R₆, —C(=NR₄)NHR₇, —C(=NR₇)OR₄, a group of formula (iv) or R₉ represents phenyl or phenyl substituted with —C₄ alkyl, $C_1$-$C_4$ haloalkyl, $C_1$-$C_4$ alkoxy, $C_1$-$C_4$ haloalkoxy, halogen, nitro or cyano;
R₁₀ represents hydrogen or methyl;
R₁₁ represents hydrogen, isopropyl, cyclopentyl, cyclopropyl, 2-butyl, 3-pentyl, 3-hydroxy-2-butyl or 2-hydroxy-3-pentyl;
m represents 0 or 1;
R₁₂ represents halogen, $C_1$-$C_4$ haloalkyl, $C_1$-$C_4$ haloalkoxy, nitro, amino, cyano, or a group of formula (i);
Y represents —CH₂— or —C(=O)—; and
Z represents NH or O;
and the salts and solvates thereof;
and a pharmaceutically acceptable carrier or diluent thereof, and optionally a second pharmaceutically active agent.

According to another aspect, the present invention provides a topical pharmaceutical composition for the treatment or prophylaxis of a fungal condition, comprising a therapeutically effective amount of a pyrimidone derivative of the general formula I, and a pharmaceutically acceptable carrier or diluent thereof, and optionally a second pharmaceutically active agent.

According to a further aspect, the present invention relates to the use of the compositions described herein for the preparation of a medicament for the treatment or prophylaxis of a fungal condition.

According to yet a further embodiment, the present invention relates to the use of the compositions described herein for the treatment or prophylaxis of a fungal condition.

According to an embodiment, the pyrimidone derivative of the general formula I is selected from the group consisting of:
(a) (1R,2R)-7-chloro-3-[2-(2,4-difluorophenyl)-2-hydroxy-1-methyl-3-(1H-1,2,4-triazol-1-yl)propyl]quinazolin-4(3H)-one;
(b) (1R,2R)-3-[2-(2,4-difluorophenyl)-2-hydroxy-1-methyl-3-(1H-1,2,4-triazol-1-yl)propyl]-7-trifluoromethylquinazolin-4(3H)-one;
(c) (1R,2R)-3-[2-(2,4-difluorophenyl)-2-hydroxy-1-methyl-3-(1H-1,2,4-triazol-1-yl)propyl]-7-(2,2,2-trifluoroethoxy)quinazolin-4(3H)-one;
(d) (1R,2R)-6-(4-chlorophenyl)-3-[2-(2,4-difluorophenyl)-2-hydroxy-1-methyl-3-(1H-1,2,4-triazol-1-yl)propyl]thieno[3,2-d]pyrimidin4(3H)-one;
(e) (1R,2R)-4-[[2-(2,4-difluorophenyl)-2-hydroxy-1-methyl-3-(1H-1,2,4-triazol-1-yl)propyl]-4-oxo-3,4-dihydrothieno[3,2-d]pyrimidin-6-yl]benzonitrile;
(f) (1R,2R)-7-(4-chlorophenoxy)-3-[2-(2,4-difluorophenyl)-2-hydroxy-1-methyl-3-(1H-1,2,4-triazol-1-yl)propyl]quinazolin-4(3H)-one;
(g) (1R,2R)-3-[2-(2,4-difluorophenyl)-2-hydroxy-1-methyl-3-(1H-1,2,4-triazol-1-yl)propyl]-6-[4-immino (methoxyamino)methyl]phenyl]thieno[3,2-d]pyrimidin4(3H)-one;
(h) (1R,2R)-7-bromo-3-[2-(2,4-difluorophenyl)-2-hydroxy-1-methyl-3-(1H-1,2,4-triazol-1-yl)propyl]quinazolin4(3H)-one;
(i) (1R,2R)-3-[2-(2,4-difluorophenyl)-2-hydroxy-1-methyl-3-(1H-1,2,4-triazol-1-yl)propyl]-7-iodoquinazolin-4(3H)-one;
(j) (1R,2R)-3-[2-(2,4-difluorophenyl)-2-hydroxy-1-methyl-3-(1H-1,2,4-triazol-1-yl)propyl]-6(4-fluorophenyl)thieno[3,2-d]pyrimidin-4(3H)-one;
(k) (1R,2R)-3-[2-(2,4-difluorophenyl)-2-hydroxy-1-methyl-3-(1H-1,2,4-triazo]-1-yl)propyl]-6-[4-(methylsulfonyl) phenyl]thieno[3,2-d]pyrimidin4(3H)-one;
(l) (1R,2R)-6-(4-fluorophenyl)-3-[2-(2-fluorophenyl)-2-hydroxy-1-methyl-3-(1H-1,2,4-triazol-1-yl)propyl]thieno[3,2-d]pyrimidin-4(3H)-one; and
(m) (1R,2R)-7-chloro-3-[2-(2-fluorophenyl)-2-hydroxy-1-methyl-3-(1H-1,2,4-triazol-1-yl)propyl]quinazolin4(3H)-one;
and a salt or solvate thereof.

According to a further embodiment, the pyrimidone derivative of general formula I is (1R,2R)-7-chloro-3-[2-(2,4-difluorophenyl)-2-hydroxy-1-methyl-3-(1H-1,2,4-triazol-1yl)propyl]quinazolin-4(3H)-one, also known as albaconazole.

The pyrimidone derivatives of general formula I useful in the present invention are further described in U.S. Pat. No. 5,807,854, the disclosure of which is incorporated herein by reference.

According to an embodiment, the pyrimidone derivative of general formula I is present in an amount from about 0.1% to about 20% by weight. In one embodiment, the pyrimidone derivative is present in an amount from about 1% to about 10% by weight. In another embodiment, the derivative is present in an amount of about 1%, 2%, 3%, 4%, 5%, 6%, 7%, 8%, 9% or 10% by weight. In a further embodiment, the pyrimidone derivative of general formula I is present in an amount of about 3% by weight.

According to another embodiment albaconazole is present in an amount from about 0.1% to about 20% by weight. In another embodiment, albaconazole is present in an amount of about 1%, 2%, 3%, 4%, 5%, 6%, 7%, 8%, 9% or 10% by weight. In a further embodiment, albaconazole is present in an amount of about 3% by weight.

The topical pharmaceutical composition comprising a pyrimidone derivative of general formula I can be formulated as a nail lacquer, enamel, paint, solution, lotion, cream, gel, aerosol foam, aerosol spray, or as any other suitable pharmaceutically acceptable topical dosage form. According to an embodiment, the pharmaceutical composition is a nail lacquer. In another embodiment the pharmaceutical composition is a nail lacquer and the prymidone derivative is albaconazole.

According to another embodiment, the pharmaceutical composition is free or substantially free of water.

Nail Lacquer

According to an embodiment, the topical pharmaceutical composition further comprises at least one volatile solvent and a film forming component. According to this embodiment, the composition is a nail lacquer. Topical application of the nail lacquer allows a flexible film to be deposited onto the affected area i.e. once the volatile solvent has evaporated. This flexible film protects the infected area from environmental stresses and/or clothing, and acts as a reservoir for the active ingredient. In one embodiment, the nail lacquer is free or substantially free of water.

Volatile Solvent

The nail lacquer of the present invention comprises one or more volatile solvents. Thus, when the nail lacquer is administered to the nail and surrounding skin of a patient, the evaporation of the volatile solvent leaves a matrix of the active ingredient within the film forming component on the surface of the nail and surrounding skin. This in turn permits the ready penetration of the active ingredient into the nail and skin.

Suitably, the volatile solvent is selected from ethanol, propyl alcohol, isopropyl alcohol, n-butyl alcohol, t-butyl alcohol, butoxy ethanol, acetone, ethyl acetate, butyl acetate, or a combination or mixture thereof. According to an embodiment, the volatile solvent is a mixture of ethanol and ethyl acetate. According to an alternative embodiment, the volatile solvent is a mixture of isopropyl alcohol and ethanol. According to an embodiment, the volatile solvent is present in an amount from about 40% to about 99.85% by weight. According to another embodiment, the volatile solvent is present in an amount from about 60% to about 90% by weight. According to yet another embodiment, the volatile solvent is present in an amount from about 75% to about 85% by weight.

Film Forming Component

According to an embodiment of the present invention, the film forming component is a film forming polymer. Suitable film forming polymers include but are not limited to, hydroxypropylmethyl cellulose, hydroxypropyl cellulose, polyvinyl pyrrolidone, carbomer, PVM/MA decadiene cross polymer, hydroxypropylguar, octylacrylamide acrylates copolymer, aminoalkyl methacrylate copolymer, ammonio methacrylate copolymer, PVP/VA copolymers, PVA, a $C_2$-$C_4$ alkyl ester of PVM/MA copolymer, shellac, or a combination or mixture thereof.

According to one embodiment, the film forming polymer is a hydrophilic polymer. Suitably, the hydrophilic polymer is selected from hydroxypropylmethyl cellulose, hydroxypropyl cellulose, polyvinyl pyrrolidone, carbomer, PVM/MA decadiene cross polymer or hydroxypropylguar, or a combination or mixture thereof.

According to an alternative embodiment, the film forming polymer is a hydrophobic polymer. Suitably, the hydrophobic polymer is selected from octylacrylamide acrylates copolymer, aminoalkyl methacrylate copolymer, ammonio methacrylate copolymer, PVP/VA copolymer, PVA, a $C_2$-$C_4$ alkyl ester of PVM/MA copolymer, or shellac, or a combination or mixture thereof.

According to an embodiment, the $C_2$-$C_4$ alkyl ester of PVM/MA copolymer is the ethyl ester, isopropyl ester or butyl ester. According to one particular embodiment, the film forming polymer is the butyl ester of PVM/MA copolymer.

In an embodiment, the film forming component is present in an amount from about 0.05% to about 40% by weight. In another embodiment, the film forming component is present in an amount from about 0.1% to about 25% by weight. According to yet another embodiment, the film forming component is present in an amount from about 10% to about 20% by weight.

For "once daily" treatment, it is preferred that a hydrophilic polymer is used as the film forming polymer. For "once weekly" treatment, it is preferred that a hydrophobic polymer is used as the film forming polymer. Use of such a hydrophobic polymer creates a water- and rub-resistant film suitable for extended treatment (i.e. less frequent application).

Additional Active Agents

According to an embodiment of the present invention, the topical pharmaceutical compositions may comprise at least one additional (or second) pharmaceutically active agent.

In an embodiment, the second pharmaceutically active agent is selected from the group consisting of an antibacterial agent, antifungal agent, corticosteroid and vitamin D analogue.

According to a further embodiment, the second pharmaceutically active agent is an antibacterial agent. Suitably, the antibacterial agent is selected from the group consisting of gentamicin, neomycin, streptomycin, cefpodoxime proxetil, clindamycin, lincomycin, erythromycin, bacitracin, gramicidin, vancomycin, doxycycline, minocycline, oxytetracycline, tetracycline, fosfomycin, fusidic acid, mupirocin, sulfacetamide, metronidazole, dapsone, triclosan, quaternary ammonium salts, silver sulfadiazine, and salts and esters thereof.

According to another embodiment, the second pharmaceutically active agent is another antifungal agent. Suitably, the antifungal agent is selected from the group consisting of echinocandins such as anidulafunin, caspofungin and micafungin; polyenes such as amphotericin B, candicidin, filipin, fungichromin, hachimycin, hamycin, lucensomycin, mepartricin, natamycin, nystatin, pecilocin, perimycin; allylamines such as butenafine, naftifine and terbinafine; imidazoles such as bifonazole, butoconazole, chlormidazole, cloconazole, clotrimazole, econazole, enilconazole, fenticonazole, flutrimazole, isoconazole, ketoconazole, lanoconazole, miconazole, neticonazole, omoconazole, oxiconazole nitrate, sertaconazole, sulconazole and tioconazole; thiocarbamates such as liranaftate, tolciclate, tolindate and tolnafate; triazoles such as pramiconazole, fluconazole, itraconazole, luliconazole, posaconazole, ravuconazole, saperconazole, terconazole and voriconazole; and other antifungal agents such as acrisorcin, amorolfine, biphenamine, bromosalicylchloranilide, buclosamide, calcium propionate, chlorphenesin, ciclopirox, cloxyquin, coparaffinate, exalamide, flucytosine, haloprogin, hexetidine, loflucarban, nifuratel, potassium iodide, propionic acid, pyrithione, salicylanilide, sodium propionate, sulbentine, tenonitrozole, triacetin, undecylenic acid, zinc propionate, griseofulvin, oligomycins, pyrrolnitrin, siccanin, viridian, and salts and esters thereof.

According to yet another embodiment, the second pharmaceutically active agent is a corticosteroid. Suitably, the corticosteroid is selected from the group consisting of alclometasone, amcinonide, beclomethasone, betamethasone, budesonide, clobetasol, clobetasone, cortisone, desonide, desoximetasone, diflorasone, diflucortolone, fluclorolone, flumethasone, fluocinolone, fluocinonide, fluocortin butyl, fluocortolone, fluprednidene, flurandrenolide, flurandrenolone, fluticasone, halcinonide, halobetasol, hydrocortisone, methylprednisolone, mometasone, prednisone, triamcinolone acetonide, prednicarbate, and salts and esters thereof.

In another embodiment, the second pharmaceutically active agent is a vitamin D analogue. Suitably, the vitamin D analogue is selected from the group consisting of calcidiol, calcitriol, calcipotriene, paricalcitol, 22-oxacolcitriol, dihydrotachysterol, calciferol, and salts and esters thereof.

The second pharmaceutically active agent is present in a therapeutically effective amount. According to an embodiment, the second pharmaceutically active agent is present in an amount from about 0.005% to about 15% by weight.

Other Ingredients

The present topical pharmaceutical compositions may comprise additional excipients, as is known in the art. Suitably, the excipient is selected from water, pH adjusting agents, humectants, film extenders, chelating agents, antioxidants, preservatives, plasticizers, penetration enhancers, fragrance, colorants, surfactants, emollients, gelling agents, radical scavengers, or a combination or mixture thereof.

pH Adjusting Agent

The present topical pharmaceutical compositions may further comprise a pH adjusting agent. In one embodiment, the pH adjusting agent is a base. Suitable pH adjusting bases include amines, bicarbonates, carbonates, and hydroxides such as alkali or alkaline earth metal hydroxides, as well as transition metal hydroxides. In another embodiment, the pH adjusting agent is an acid, an acid salt, or mixtures thereof. According to yet another embodiment, the pH adjusting agent is a buffer. Suitably, the buffer is selected from citrate/citric acid, acetate/acetic acid, phosphate/phosphoric acid, formate/formic acid, propionate/propionic acid, lactate/lactic acid, carbonate/carbonic acid, ammonium/ammonia, edetate/edetic acid, or a combination or mixture thereof.

According to an embodiment, the pH adjusting agent is present in an amount from about 0.01% to about 10% by weight. According to another embodiment, the pH adjusting agent is present in an amount sufficient to adjust the pH of the composition to between about 4 to about 6.5.

Humectants

The present topical pharmaceutical compositions may further comprise a humectant. Non-limiting examples of humectants useful in this regard include glycerol, sorbitol, maltitol, polydextrose, triacetin, propylene glycol, polyethylene glycol (PEG) esters including PEG-20 stearate, PEG-40 stearate, PEG-150 stearate, PEG-150 distearate and PEG-100 stearate, alkoxylated alcohols including laureth-12, ceteareth-20, laureth-23, glycereth-7, glycereth-12, glycereth-26, PEG-4, PEG-6, PEG-8, PEG-12, PEG-32, PEG-75, PEG-150, or a combination or mixture thereof. In an embodiment, the humectant is glycerol.

In an embodiment, the present compositions comprise about 0.1% to about 10% by weight of a humectant. In a further embodiment, the present compositions comprise about 0.5% to about 5% by weight of a humectant.

Film Extenders

The present topical pharmaceutical compositions may further comprise at least one film extender. Non-limiting examples of film extenders useful in this regard include calcium carbonate, calcium phosphate, calcium stearate, magnesium stearate, zinc stearate, calcium sulfate, colloidal silicon dioxide, kaolin, magnesium carbonate, magnesium silicate, sodium stearyl fumarate, talc, titanium dioxide, zinc oxide, or a combination or mixture thereof. In an embodiment, the film extender is present in an amount from about 0.1% to about 2% by weight.

Chelating Agents

The present topical pharmaceutical compositions may further comprise a chelating agent. Non-limiting examples of chelating agents useful in this regard include citric acid, isopropyl (mono) citrate, stearyl citrate, lecithin citrate, gluconic acid, tartaric acid, oxalic acid, phosphoric acid, sodium tetrapyrophosphate, potassium monophosphate, sodium hexametaphosphate, calcium hexametaphosphate, sorbitol, glycine (aminoacetic acid), methyl glucamine, triethanolamine (trolamine), EDTA, DEG (dihydroxyethylglycine), DPTA (diethylene triamine pentaacetic acid), NTA (nitrilotriacetic acid), HEDTA (N-(hydroxyethyl)-ethylenetriaminetriacetic acid), aminocarboxylates, dimercaperol (BAL), larixinic acid (maltol), unidentate ligands (fluoride and cyanide ions), diphenylthiocarbazone, o-phenanthroline, barium diphenylamine sulfonate, sodium glucoheptonate, 8-hydroxyquinoline, olefin complexes (such as dicyclopentadienyl iron), porphyrins, phosponates, or a combination or mixture thereof. In an embodiment, the chelating agent is present in an amount from about 0.1% to about 1% by weight.

Antioxidants

The present topical pharmaceutical compositions may further comprise an antioxidant. Non-limiting examples of substances which can serve as the antioxidant herein include butylated hydroxytoluene, butylated hydroxyanisole, tocopherol, propyl gallate, vitamin E TPGS, or a combination or mixture thereof. In an embodiment, the present compositions comprise an antioxidant in an amount from about 0.001% to about 1% by weight.

Preservatives

The present topical pharmaceutical compositions may further comprise a preservative. Non-limiting examples of substances which can serve as the preservative herein include benzyl alcohol, diazolidinyl urea, methyl paraben, ethyl paraben, propyl paraben, butyl paraben, phenoxyethanol, sorbic acid, benzoic acid, salts thereof, or a combination or mixture thereof. In an embodiment, the present compositions comprise a preservative in an amount from about 0.01% to about 2% by weight.

Methods of Treatment

The present topical compositions are particularly effective in treating the specific dermatophyte *Trichophyton rubrum*. According to an embodiment, the present invention relates to a method of treating a fungal condition caused by a *Trichophyton rubrum* infection. The present compositions are also effective in treating fungal conditions caused by *Trichophyton mentagrophytes* and *Epidermophyton floccosum*.

In one embodiment, the fungal condition is selected from the group consisting of onychomycosis, tinea pedis (athlete's foot), tinea cruris (groin), tinea barbae (beard), tinea capitis (scalp), tinea corporis (body), tinea manuum (hand) and dermatophytosis (ringworm).

According to one embodiment, the fungal condition is onychomycosis.

Combination Therapy

In another embodiment, the present topical compositions may be used in combination with an additional (separate) dosage form to enhance the treatment of the fungal condition. This additional dosage form may be applied or taken at the same time as the present compositions i.e. concomitantly. Alternatively, one of the present compositions and the additional dosage form is administered in the morning and the other is administered in the evening (or vice versa).

In an embodiment, the present topical composition is administered as a combination with a separate oral composition containing an antifungal agent, which may be the same or different to the pyrimidone derivatives of general formula I described herein. In an embodiment, the antifungal agent in the oral composition is selected from terbinafine, pramiconazole, itraconazole, griseofulvin or fluconazole. In an alternative embodiment, the antifungal agent in the oral composition is a pyrimidone derivative of the general formula I. According to a further embodiment, the pyrimidone derivative of the general formula I in the oral composition is albaconazole.

According to another embodiment, the present topical pharmaceutical compositions are used as a maintenance therapy. Maintenance therapy is initiated following substantial or complete alleviation of the symptoms of the fungal condition following primary treatment.

In an embodiment, the composition for maintenance therapy is a nail lacquer comprising a pyrimidone derivative of general formula I. According to a further embodiment, the pyrimidone derivative of general formula I is albaconazole.

One embodiment of the invention is a nail lacquer composition for topical administration, comprising a therapeutically effective amount of albaconazole and at least one volatile solvent and a film forming component, an optionally at least one additional pharmaceutically acceptable active agent.

In another embodiment the composition includes at least one volatile solvent is selected from the group consisting of ethanol, propyl alcohol, isopropyl alcohol, n-butyl alcohol, t-butyl alcohol, butoxy ethanol, acetone, ethyl acetate and butyl acetate.

In another embodiment the at least one volatile solvent is a mixture of isopropyl alcohol and ethanol.

In another embodiment the at least one volatile solvent is a mixture of ethyl acetate and ethanol.

In another embodiment the film forming component is a film forming polymer selected from the group consisting of hydroxypropylmethyl cellulose, hydroxypropyl cellulose, polyvinyl pyrrolidone, carbomer, PVM/MA decadiene cross polymer, hydroxypropylguar, octylacrylamide acrylates copolymer, aminoalkyl methacrylate copolymer, ammonio methacrylate copolymer, PVP/VA copolymers, PVA, a $C_2$-$C_4$ alkyl ester of PVM/MA copolymer, shellac and mixtures thereof.

In another embodiment the film forming component is the butyl ester of PVM/MA copolymer.

In another embodiment the one or more additional excipients to the topical dosage form is selected from the group consisting of water, pH adjusting agents, humectants, film extenders, chelating agents, antioxidants, preservatives, plasticizers, penetration enhancers, fragrance, colorants, surfactants, emollients, gelling agents, and radical scavengers.

In another embodiment the composition may comprise at least one second pharmaceutically active agent selected from the group consisting of an antibacterial agent, antifungal agent, corticosteroid and vitamin D analogue.

Definitions

As used herein, the terms "administered", "administering" and "administration," refer to any method which, in sound medical practice, delivers the composition to a patient in such a manner as to provide a therapeutic effect.

It should be understood that the terms "a" and "an" as used above and elsewhere herein refer to "one or more" of the enumerated components. It will be clear to one of ordinary skill in the art that the use of the singular includes the plural unless specifically stated otherwise.

Throughout the application, descriptions of various embodiments use "comprising" language, however it will be understood by one of skill in the art, that in some specific instances, an embodiment can alternatively be described using the language "consisting essentially of" or "consisting of".

As used herein, the phrases an "effective amount" or a "therapeutically effective amount" of an active agent or ingredient, or pharmaceutically active agent or ingredient, which are synonymous herein, refer to an amount of the pharmaceutically active agent sufficient to have a therapeutic effect upon administration. A therapeutically effective amount of the pharmaceutically active agent may, will, or is expected to treat the fungal condition. Effective amounts of the pharmaceutically active agent will vary with the particular condition being treated, the severity of the condition, the duration of the treatment, and the specific components of the composition being used.

As used herein, the term "matrix" means the space within the crosslinked polymer structure. This space also serves as a "reservoir" wherein the active ingredient or ingredients reside prior to administration.

As used herein, the term "salts thereof" refers to salts that are pharmaceutically acceptable and that possess the desired pharmacological activity of the parent compound. Such salts include: (1) acid addition salts, formed with acids such as, for example, acetic acid, benzoic acid, citric acid, gluconic acid, glutamic acid, glutaric acid, glycolic acid, hydrochloric acid, lactic acid, maleic acid, malic acid, malonic acid, mandelic acid, phosphoric acid, propionic acid, sorbic acid, succinic acid, sulfuric acid, tartaric acid, naturally and synthetically derived amino acids, and mixtures thereof; or (2) salts formed when an acidic proton present in the parent compound is either (i) replaced by a metal ion e.g. an alkali metal ion, an alkaline earth metal ion, or an aluminium ion; or (ii) protonates an organic base such as, for example, ethanolamine, diethanolamine, triethanolamine, tromethamine and N-methylglucamine.

As used herein, the term "substantially free" of a specified component refers to a composition with less than about 1% of the specified component.

As used herein, a "treatment" or "treating" of a condition encompasses alleviation of at least one symptom thereof, a reduction in the severity thereof, or the delay, prevention or inhibition of the progression thereof. Treatment need not mean that the condition is totally cured. A useful composition herein need only reduce the severity of a condition, reduce the severity of symptoms associated therewith, provide improvement to a patient's quality of life, or delay, prevent or inhibit the onset of a condition.

For the purposes of better understanding the present teachings and in no way limiting the scope thereof, unless otherwise indicated, all numbers expressing quantities, percentages or proportions, and other numerical values used in the specification and claims, are to be understood as being modified in all instances by the term "about".

Other terms as used herein are meant to be defined by their well-known meanings in the art. Unless defined otherwise, all technical and scientific terms used herein have the same meaning as commonly understood to one of ordinary skill in the art to which the presently described invention pertains.

The following Examples are illustrative of the present invention and are not intended to be limitations thereof.

BIOLOGICAL EXAMPLES

Microdilution Assay

Multiple strains of *Trichophyton rubrum*, *Trichophyton mentagrophytes* and *Epidermophyton flucossum* were obtained from the culture collection facility at the Center for Medical Mycology (University Hospitals of Cleveland/Case Western Reserve University, Cleveland, Ohio). The minimum inhibitory concentration (MICs) for albaconazole, ciclopirox and terbinafine against each dermatophyte strain was determined according to the method approved by the CLSI Antifungal Subcommittee as a reference method for determining dermatophyte susceptibilities (Ghannoum et al., *J. Clin. Microbiol.* 42: 2977-2979, 2004). In addition, the minimum fungicidal concentration (MFCs) for the active agents against each dermatophyte strain was determined according to the modifications suggested by Canton et al., *Diagn. Microbiol. Infect. Dis.* 45:203-206, 2003.

Tables 1 and 2 describe the minimum inhibitory concentrations (in ug/mL) and the minimum fungicidal concentrations (in ug/mL), respectively, for the active agents against the dermatophyte strains. Overall, MICs and MFCs for albaconazole were lower than those for ciclopirox and similar to those for terbinafine. However, albaconazole was more effective against terbinafine-resistant *Trichophyton rubrum* strains. Thus, the data demonstrates that albaconazole has significant potency across a range of dermatophyte strains that are associated with onychomycosis, including isolates that are resistant to terbinafine.

TABLE 1

|  | Albaconazole | Ciclopirox | Terbinafine |
|---|---|---|---|
| *T. mentagrophytes* | | | |
| Range (n = 5) | 0.12-0.5 | 0.12-0.25 | 0.002-0.004 |
| $MIC_{50}$ | 0.12 | 0.25 | 0.002 |
| $MIC_{90}$ | 0.5 | 0.25 | 0.004 |
| *T. rubrum* | | | |
| Range (n = 2) | 0.06 | 0.12 | 0.002 |
| $MIC_{50}$ | 0.06 | 0.12 | 0.002 |
| $MIC_{90}$ | 0.06 | 0.12 | 0.002 |
| *T. rubrum* elevated terbinafine (MIC) | | | |
| Range (n = 3) | 0.015-0.25 | 0.12 | 8-32 |
| $MIC_{50}$ | 0.06 | 0.12 | 8 |
| $MIC_{90}$ | 0.25 | 0.12 | 32 |
| *E. flucossum* | | | |
| Range (n = 5) | 0.008-0.015 | 0.12 | 0.002-0.008 |
| $MIC_{50}$ | 0.015 | 0.12 | 0.002 |
| $MIC_{90}$ | 0.015 | 0.12 | 0.008 |

TABLE 1-continued

|  | Albaconazole | Ciclopirox | Terbinafine |
|---|---|---|---|
| All Dermatophytes | | | |
| Range (n = 15) | 0.008-0.5 | 0.12-025 | 0.002-32 |
| $MIC_{50}$ | 0.06 | 0.12 | 0.002 |
| $MIC_{90}$ | 0.25 | 0.25 | 8 |

TABLE 2

|  | Albaconazole | Ciclopirox | Terbinafine |
|---|---|---|---|
| *T. mentagrophytes* | | | |
| Range (n = 5) | 0.5-8 | 0.5->32 | 0.015-0.03 |
| $MFC_{50}$ | 1 | >32 | 0.015 |
| $MFC_{90}$ | 8 | >32 | 0.03 |
| *T. rubrum* | | | |
| Range (n = 2) | 0.5-8 | 16-32 | 0.008 |
| $MFC_{50}$ | 0.5 | 16 | 0.008 |
| $MFC_{90}$ | 8 | 32 | 0.008 |
| *T. rubrum* elevated terbinafine (MIC) | | | |
| Range (n = 3) | 0.06-1 | 0.25->32 | 16->64 |
| $MFC_{50}$ | 0.25 | 16 | 32 |
| $MFC_{90}$ | 1 | >32 | >64 |
| *E. flucossum* | | | |
| Range (n = 5) | 0.06-8 | 0.25->32 | 0.15-0.03 |
| $MFC_{50}$ | 0.25 | 4 | 0.03 |
| $MFC_{90}$ | 8 | >32 | 0.03 |
| All Dermatophytes | | | |
| Range (n = 15) | 0.06-8 | 0.25->32 | 0.008 |
| $MFC_{50}$ | 0.5 | 16 | 0.015 |
| $MFC_{90}$ | 8 | >32 | 32 |

Nail Drilling Model

Full thickness circular nail sections (3.9 mm diameter) were placed on cotton wool pads moistened with water (32° C.) and albaconazole lacquer formulations were applied once daily for up to 14 days. At the end of the incubation period, individual nail sections were glued onto a Petri dish base and drilled using a Dremel 3891 professional series drill (starting with ventral side up). Drilling depth was controlled and used to define ventral, intermediate and dorsal regions. Fine nail powder was collected and albaconazole was extracted and measured using an HPLC method (LOQ=0.012 μg/mL) in order to determine the extent of penetration of albaconazole through the nail (following topical application).

Figure 1:
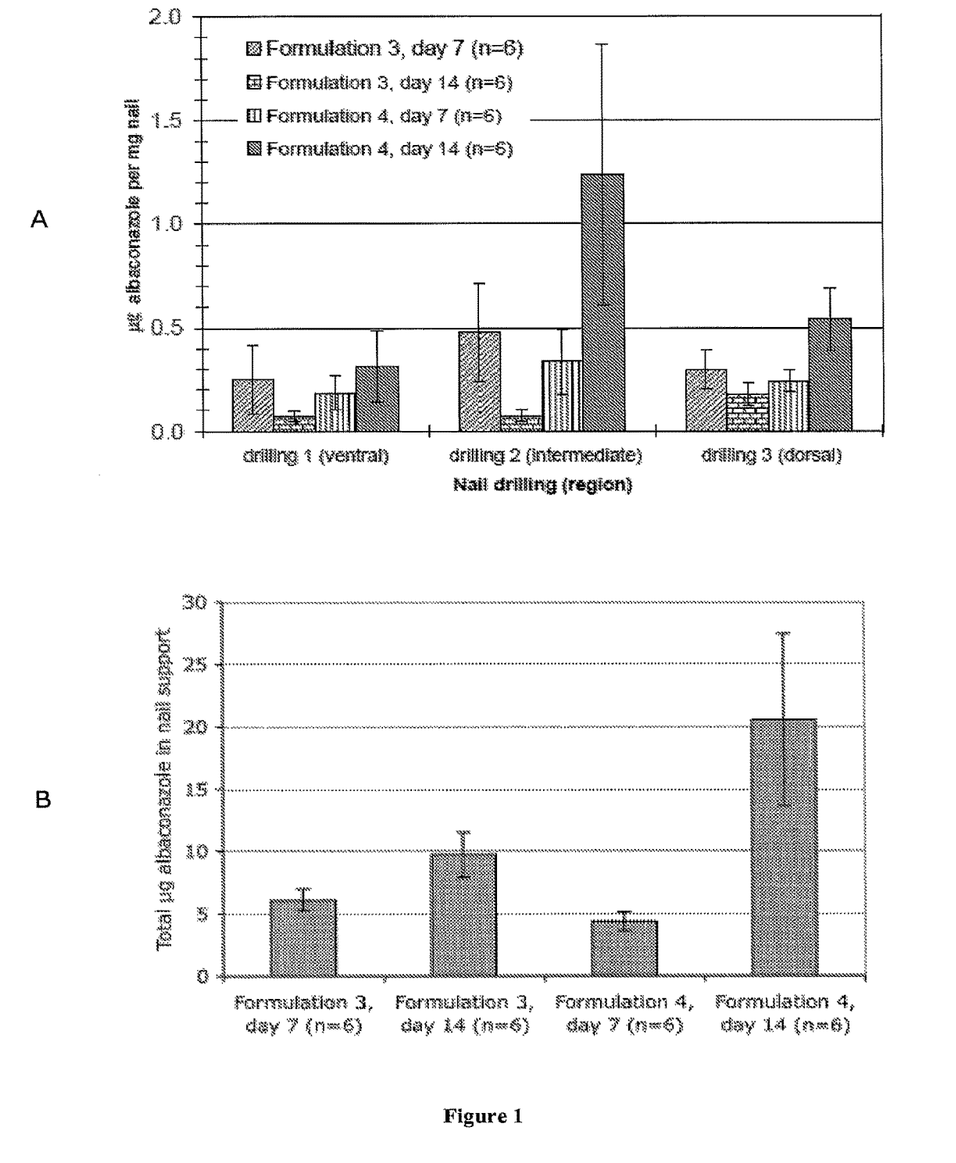
FIG. 1 illustrates the distribution of albaconazole in (A) nail drillings and (B) receptor pads (nail supports).

FIG. 1 illustrates the distribution of albaconazole in (A) nail drillings and (B) receptor pads following daily topical application of Formulations 3 and 4 (Table 3). Significant amounts of albaconazole were found in the ventral section of the nail, as well as the receptor pad. Therefore, the data illustrates that when the compositions of the present invention are applied topically, the active agent (albaconazole) significantly penetrates the nail to where the dermatophytes reside. Data is presented as mean+/−SD, n=6.

TABLE 3

| Formulation 3 | w/w % | Formulation 4 | w/w % |
|---|---|---|---|
| albaconazole | 3 | albaconazole | 3 |
| ethyl acetate | 34 | ethyl acetate | 34 |

TABLE 3-continued

| Formulation 3 | w/w % | Formulation 4 | w/w % |
| --- | --- | --- | --- |
| ammonio methacrylate copolymer (Eudragit RL100) | 15 | butyl ester of PVM/MA copolymer (Gantrez ES-425) | 29 |
| ethanol (anhydrous) | 48 | ethanol (anhydrous) | 34 |
| Total | 100 | Total | 100 |

(Note that Gantrez ES-425 is supplied as a 50% solution in ethanol i.e. 29% Gantrez ES-425 is equivalent to 14.5% polymer resin. Thus, Formulation 4 describes a composition with 3% albaconazole, 34% ethyl acetate, 48.5% ethanol and 14.5% film forming substance.)

Infected Nail Model

Full thickness cadaver nail sections (3 mm$^2$) were inoculated with *Trichophyton rubrum* on the ventral side and incubated for 14 days at 25° C. to allow infection. Thereafter, albaconazole lacquer (Table 4) and PENLAC® (ciclopriox) nail lacquer solutions were applied to the dorsal side of the nail section once weekly for 2 weeks. At the end of the dosing period, excess formulation was removed from the surface of the nail, and the viability of *Trichophyton rubrum* was assessed based on the presence of ATP.

Figure 2:
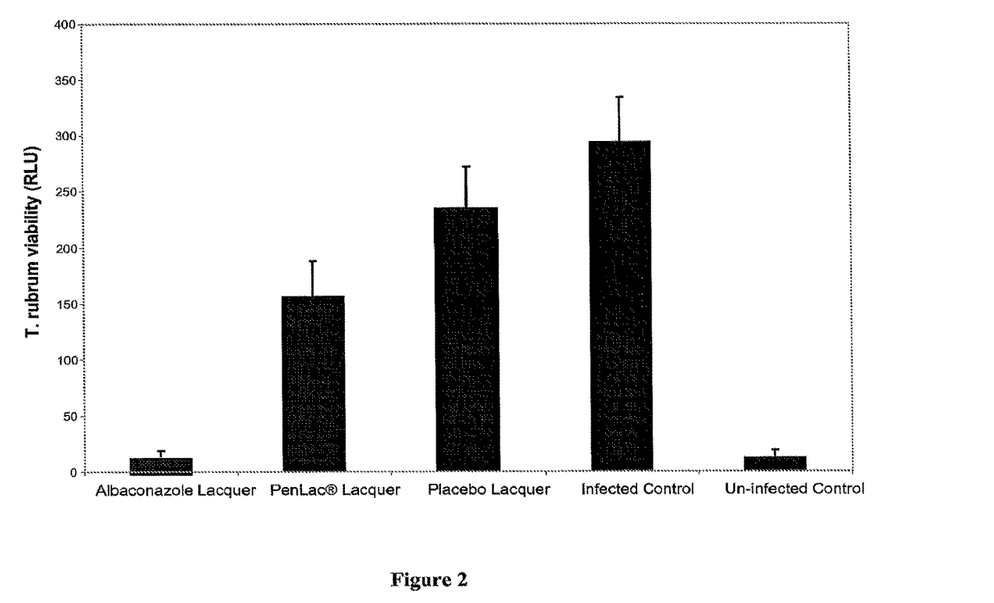
FIG. 2 illustrates the results of an Infected Nail Assay which compares the effectiveness of a composition according to the present invention with a commercial comparator (PENLAC® nail lacquer), in reducing the viability of *Trichophyton rubrum*.

FIG. 2 describes a comparison of the fungal cell viability (as measured by ATP release) following once weekly topical application of antifungal lacquer formulations for two weeks. Infected controls (*Trichophyton rubrum*-infected, no treatment) and uninfected controls (background) were included in parallel. Ciclopriox was only mildly effective. On the other hand, albaconazole lacquer was highly effective, reducing fungal cell viability down to background levels. This data suggests that following topical application, albaconazole has greater efficacy compared to ciclopirox in eradicating *Trichophyton rubrum*-infected full thickness human nails. Data is presented as mean+/−SEM, n=6.

FORMULATION EXAMPLE

The following example illustrates a nail lacquer composition of the present invention, with % w/w provided. The nail lacquer is suitable for use in the primary treatment of onychomycosis, or as a maintenance therapy.

TABLE 4

| Component | w/w % |
| --- | --- |
| albaconazole | 3 |
| ethyl acetate | 31 |
| butyl ester of PVM/MA copolymer (Gantrez ES-425) | 29 |
| ethanol (anhydrous) | 37 |
| Total | 100 |

(Note that Gantrez ES-425 is supplied as a 50% solution in ethanol i.e. 29% Gantrez ES-425 is equivalent to 14.5% polymer resin. Thus, the composition comprises 3% albaconazole, 31% ethyl acetate, 51.5% ethanol and 14.5% film forming substance.)

The composition was prepared by adding the active ingredient to ethanol while mixing. The ethyl acetate was then added with continuous mixing. The Gantrez ES-425 was then added, while mixing until the composition became clear. Alternatively, the ethanol, ethyl acetate and Gantrez ES-425 were mixed until the composition became clear. The active ingredient was then added whilst mixing until the composition became clear.

Although specific embodiments of the invention have been described above, it will be clear to the skilled addressee that the invention is not restricted to these particular embodiments, and variations of the invention may be made without departing from the scope of the present invention.

What is claimed is:

1. A method for the treatment of a fungal condition in a patient and the utilization of a maintenance therapy thereafter, the method comprising topically applying to the patient a nail lacquer comprising a pharmaceutically acceptable composition of a therapeutically effective amount of a pyrimidone derivative of the general formula I:

as a racemate, a diastereomer mixture or as a pure enantiomer, wherein:

Ar represents phenyl or phenyl substituted with one or more halogen and/or trifluoromethyl groups;

$R_1$ is $C_1$-$C_4$ alkyl;

$R_2$ is hydrogen or $C_1$-$C_4$ alkyl; or $R_1$ together with $R_2$ form a $C_2$-$C_4$ polymethylene chain;

$R_3$ represents hydrogen, $C_1$-$C_4$ alkyl, $C_1$-$C_4$ haloalkyl, or cyclopropyl;

A represents a benzene ring or a 5- or 6-membered heterocyclic ring wherein one or more of the ring atoms are selected from the group consisting of N, O and S, which rings can be optionally fused to a benzene ring or to a 5- or 6-membered heterocyclic ring containing one or more heteroatoms selected from N, O and S, and wherein A can be unsubstituted or have 1, 2, 3 or 4 groups W on any of the rings;

the group W represents $C_1$-$C_4$ alkyl, $C_3$-$C_6$ cycloalkyl, $C_1$-$C_4$ haloalkyl, $C_1$-$C_4$ alkoxy, $C_1$-$C_4$ haloalkoxy, halogen, nitro, cyano, hydroxy, benzyloxy, hydroxymethyl, a group —$NR_4R_5$, a group —$CONR_4R_5$, a group —$CH_2$—OCO—$R_4$, a group —CO—$R_4$, a group —COO—$R_4$, a group —$SO_zR_6$, a group —C(=$NR_4$)$NHR_7$, a group —C(=$NR_7$)$OR_4$, and additionally one of the groups W can also represent 1-pyrrolyl, 1-imidazolyl, H-1,2,4-triazol-1-yl, 5-tetrazolyl (optionally substituted with $C_1$-$C_4$ alkyl), 1-pyrrolidinyl, 4-morpholinyl, 4-morpholinyl-N-oxide, a group —X—$R_8$, or a group of formula (i)-(iv):

(i)

-continued wherein:
R$_4$ represents hydrogen, C$_1$-C$_4$ alkyl, C$_3$-C$_6$ cycloalkyl or arylC$_{1-4}$ alkyl, wherein aryl represents phenyl or phenyl substituted with one or more C$_1$-C$_4$ alkyl, halogen, C$_1$-C$_4$ haloalkyl, C$_1$-C$_4$ alkoxy or C$_1$-C$_4$ haloalkoxy groups;
R$_5$ represents hydrogen, C$_1$-C$_4$ alkyl, C$_3$-C$_6$ cycloalkyl, a group —COR$_4$ or a group —COCF$_3$;
R$_6$ represents C$_1$-C$_4$ alkyl;
z represents 0, 1 or 2;
R$_7$ represents hydrogen, —CONH$_2$, —COMe, —CN, —SO$_2$NHR$_4$, —SO$_2$R$_4$, —OR$_4$, —OCOR$_4$ or —(C$_{1-4}$ alkyl)-NH$_2$;
X represents a single bond, —O—, —SOz, —NR$_4$—, or —C(=O)—;
R$_8$ represents a phenyl group optionally substituted with one or more groups R$_9$;
R$_9$ represents C$_1$-C$_4$ alkyl, C$_3$-C$_6$ cycloalkyl, C$_1$-C$_4$ haloalkyl, C$_1$-C$_4$ alkoxy, C$_1$-C$_4$ haloalkoxy, halogen, nitro, cyano, a group —NR$_4$R$_5$, a group —CONR$_4$R$_5$, a group —CH$_2$—OCO—R$_4$, a group —CO—R$_4$, a group —COO—R$_4$, a group —SO$_z$R$_6$, a group —C(=NR$_4$)NHR$_7$, a group —C(=NR$_7$)OR$_4$, a group of formula (iv) or R$_9$ represents a phenyl group (optionally substituted with a group C$_1$-C$_4$ alkyl, C$_1$-C$_4$ haloalkyl, C$_1$-C$_4$ alkoxy, C$_1$-C$_4$ haloalkoxy, halogen, nitro or cyano);
R$_{10}$ represents hydrogen or methyl;
R$_{11}$ represents hydrogen, isopropyl, cyclopentyl, cyclopropyl, 2-butyl, 3-pentyl, 3-hydroxy-2-butyl, or 2-hydroxy-3-pentyl;
m represents 0 or 1;
R$_{12}$ represents halogen, C$_1$-C$_4$ haloalkyl, C$_1$-C$_4$ haloalkoxy, nitro, amino, cyano, or a group of formula (i);
Y represents —CH$_2$— or —C(=O)—; and
Z represents NH or 0;
and salts thereof;
a pharmaceutically acceptable carrier or diluent thereof, at least one volatile solvent, and a film forming component; wherein the composition does not include a penetration enhancer; wherein the pyrimidone derivative is the only pharmaceutically active agent present in the nail lacquer; and wherein the maintenance therapy is initiated following treatment of the fungal condition.

2. The method according to claim 1, wherein the pyrimidone derivative of the general formula I is selected from the group consisting of:
(a) (1R,2R)-7-chloro-3-[2-(2,4-difluorophenyl)-2-hydroxy-1-methyl-3-(1H-1,2,4-triazol-1-yl)propyl]quinazolin-4(3H)-one;
(b) (1R,2R)-3-[2-(2,4-difluorophenyl)-2-hydroxy-1-methyl-3-(1H-1,2,4-triazol-1-yl)propyl]-7-trifluoromethylquinazolin-4(3H)-one;
(c) (1R,2R)-3-[2-(2,4-difluorophenyl)-2-hydroxy-1-methyl-3-(1H-1,2,4-triazol-1-yl)propyl]-7-(2,2,2-trifluoroethoxy) quinazolin-4(3H)-one;
(d) (1R,2R)-6-(4-chlorophenyl)-3-[2-(2,4-difluorophenyl)-2-hydroxy-1-methyl-3-(1H-1,2,4-triazol-1-yl)propyl]thieno[3,2-d]pyrimidin4(3H)-one;
(e) (1R,2R)-4-[[2-(2,4-difluorophenyl)-2-hydroxy-1-methyl-3-(1H-1,2,4-triazol-1-yl)propyl]-4-oxo-3,4-dihydrothieno[3,2-d]pyrimidin-6-yl]benzonitrile;
(f) (1R,2R)-7-(4-chlorophenoxy)-3-[2-(2,4-difluorophenyl)-2-hydroxy-1-methyl-3-(1H-1,2,4-triazol-1-yl)propyl]quinazolin-4(3H)-one;
(g) (1R,2R)-3-[2-(2,4-difluorophenyl)-2-hydroxy-1-methyl-3-(1H-1,2,4-triazol-1-yl)propyl]-6-[4-immino (methoxyamino)methyl]phenyl]thieno[3,2-d]pyrimidin4(3H)-one;
(h) (1R,2R)-7-bromo-3-[2-(2,4-difluorophenyl)-2-hydroxy-1-methyl-3-(1H-1,2,4-triazol-1-yl)propyl]quinazolin4(3H)-one;
(i) (1R,2R)-3-[2-(2,4-difluorophenyl)-2-hydroxy-1-methyl-3-(1H-1,2,4-triazol-1-yl)propyl]-7-iodoquinazolin-4(3H)-one;
(j) (1R,2R)-3-[2-(2,4-difluorophenyl)-2-hydroxy-1-methyl-3-(1H-1,2,4-triazol-1-yl)propyl]-6(4-fluorophenyl) thieno[3,2-d]pyrimidin-4(3H)-one;
(k) (1R,2R)-3-[2-(2,4-difluorophenyl)-2-hydroxy-1-methyl-3-(1H-1,2,4-triazo]-1-yl)propyl]-6-[4-(methylsulfonyl)phenyl]thieno[3,2-d]pyrimidin-4(3H)-one;
(l) (1R,2R)-6-(4-fluorophenyl)-3-[2-(2-fluorophenyl)-2-hydroxy-1-methyl-3-(1H-1,2,4-triazol-1-yl)propyl] thieno[3,2-d]pyrimidin-4(3H)-one; and
(m) (1R,2R)-7-chloro-3-[2-(2-fluorophenyl)-2-hydroxy-1-methyl-3-(1H-1,2,4-triazol-1-yl)propyl]quinazolin-4 (3H)-one;
and a salt thereof; and a solvate thereof.

3. The method according to claim 1, wherein the pyrimidone derivative of general formula I is (1R,2R)-7-chloro-3-[2-(2,4-difluorophenyl)-2-hydroxy-1-methyl-3-(1H-1,2,4-triazol-1yl)propyl]quinazolin-4(3H)-one, a pharmaceutically acceptable salt thereof, or a solvate thereof.

4. The method according to claim 1, wherein the pyrimidone derivative of general formula I is present in an amount from about 0.1% to about 20% by weight.

5. The method according to claim 1, wherein the pyrimidone derivative of general formula I is present in an amount from about 1% to about 10% by weight.

6. The method according to claim 1, wherein the pyrimidone derivative of general formula I is present in an amount of about 3% by weight.

7. The method according to claim 1, wherein the at least one volatile solvent is selected from the group consisting of ethanol, propyl alcohol, isopropyl alcohol, n-butyl alcohol, t-butyl alcohol, butoxy ethanol, acetone, ethyl acetate and butyl acetate.

8. The method according to claim 1, wherein the at least one volatile solvent is a mixture of isopropyl alcohol and ethanol.

9. The method according to claim 1, wherein the at least one volatile solvent is a mixture of ethyl acetate and ethanol.

10. The method according to claim 1, wherein the film forming component is a film forming polymer selected from the group consisting of hydroxypropylmethyl cellulose, hydroxypropyl cellulose, polyvinyl pyrrolidone, carbomer, PVM/MA decadiene cross polymer, hydroxypropylguar, octylacrylamide acrylates copolymer, aminoalkyl methacrylate copolymer, ammonia methacrylate copolymer, PVP/VA copolymers, PVA, a $C_2$-$C_4$ alkyl ester of PVM/MA copolymer, shellac and mixtures thereof.

11. The method according to claim 1, wherein the film forming component is the butyl ester of PVM/MA copolymer.

12. The method according to claim 1, wherein the composition further comprises one or more excipients selected from the group consisting of water, pH adjusting agents, humectants, film extenders, chelating agents, antioxidants, preservatives, plasticizers, fragrance, colorants, surfactants, emollients, gelling agents, radical scavengers, and mixtures thereof.

13. The method according to claim 1, wherein the fungal condition is a fungal condition caused by a *Trichophyton rubrum* infection.

14. The method according to claim 1, wherein the fungal condition is selected from the group consisting of onychomycosis, tinea pedis, tinea cruris, tinea barbae, tinea capitis, tinea corporis, tinea manuum and dermatophytosis.

15. The method according to claim 14, wherein the fungal condition is onychomycosis.

16. The method according to claim 1, Wherein the pyrimidone derivative of formula (I) is albaconazole.

* * * * *